United States Patent [19]

Suhadolnik et al.

[11] Patent Number: 4,708,935
[45] Date of Patent: Nov. 24, 1987

[54] (2-5')-OLIGO (3'-DEOXYADENYLATE) AND DERIVATIVES THEREOF

[75] Inventors: Robert J. Suhadolnik, Roslyn, Pa.; Joseph M. Wu, Mohegan Lake, N.Y.; Paul Doetsch, Beltsville, Md.; Earl E. Henderson, Elkins Park, Pa.

[73] Assignee: Research Corporation, New York, N.Y.

[21] Appl. No.: 717,709

[22] Filed: Mar. 29, 1985

Related U.S. Application Data

[62] Division of Ser. No. 605,004, Apr. 27, 1984, Pat. No. 4,539,313, which is a division of Ser. No. 252,926, Apr. 10, 1981, Pat. No. 4,464,359.

[51] Int. Cl.[4] .................. C12P 19/34; C12P 19/36; C12N 9/12
[52] U.S. Cl. ........................................ 435/91; 435/90; 435/194
[58] Field of Search .................... 435/91, 90, 194

[56] References Cited

U.S. PATENT DOCUMENTS

| | | | |
|---|---|---|---|
| 2,472,130 | 6/1949 | Szent-Gyorgyi | 536/27 |
| 3,299,043 | 1/1967 | Schramm et al. | 536/27 |
| 3,337,530 | 8/1967 | Hanze | 536/28 |
| 4,000,260 | 12/1976 | Prusoff et al. | 536/23 |
| 4,210,746 | 7/1980 | Kerr et al. | 536/27 |
| 4,315,001 | 2/1982 | Blough | 424/180 |
| 4,378,352 | 3/1983 | Kimchi et al. | 536/27 |

Primary Examiner—Lionel M. Shapiro
Attorney, Agent, or Firm—Scully, Scott, Murphy & Presser

[57] ABSTRACT

3'-deoxyadenosine 5'-triphosphate is oligomerized to form (2'-5')-oligo (3'-deoxyadenylate) by incubation with adenosine triphosphate: (2'-5')-oligo adenosine adenyl transferase, in the presence of an inert support carrying a double straded polynucleotide. The (2'-5')-oligo (3'-deoxyadenylate) is digested with a suitable phosphatase to remove the terminal phosphate groups. The thus produced corresponding 3'-deoxyadenosine compound is an anti-viral material effective against Herpes Simplex infection and effective in inhibiting the transformation of cells infected with Epstein Barr virus.

5 Claims, 3 Drawing Figures

(2'-5')-OLIGO (3'-DEOXYADENYLATE) AND DERIVATIVES THEREOF

This is a divisional of copending application Ser. No. 605,004, filed on Apr. 27, 1984, now U.S. Pat. No. 4,539,313, issued Sept. 3, 1985, which was a divisional of application Ser. No. 252,926 filed on Apr. 10, 1981, now U.S. Pat. No. 4,464,359, issued Aug. 7, 1984.

BACKGROUND OF THE INVENTION

1. Field of the Invention

There are provided oligomers of 3'-deoxyadenosine-5'-triphosphate and the terminally dephosphorylated analogs thereof which are useful anti-viral agents and methods for producing said materials.

2. Discussion of the Relevant Art

The full nomenclature of the subject matter of the present invention involves extremely long terms. It is customary for those skilled in the art to abbreviate these terms in a manner well known to them. These general and customary abbreviations are set forth herein below and will be utilized in the text of this specification.

Abbreviations: EBV, Epstein Barr virus; $(2'-5')(A)_n$ synthetase, ATP: $(2'-5')$oligo(A) adenyltransferase (EC 2.7.7.-); $(2'-5')$pppA(pA)$_n$ or $(2'-5')$oligo(A), oligomer of adenylic acid with $(2'-5')$-phosphodiester linkages and a triphosphate at the 5'-end; $(2'-5')$-ppp3'dA(p3'dA)$_n$, oligomer of 3'-deoxyadenylic acid with $(2'-5')$-phosphodiester linkages and a triphosphate at the 5'-end; $(2'-5')$A(pA)$_n$ or core oligomer, oligomer of adenylic acid with $(2'-5')$-phosphodiester linkages; $(2'-5')$A(pA)$_2$ or core trimer, adenylyl$(2'-5')$adenylyl$(2'-5')$adenosine; $(2'-5')$A(pA)$_3$ or core tetramer, adenylyl$(2'-5')$ adenylyl$(2'-5')$adenylyl $(2'-5')$adenosine; $(2'-5')$3'dA(p3'dA)$_2$ or core trimer analog, 3'-deoxyadenylyl $(2'-5')$3'-deoxyadenylyl$(2'-5')$3'-deoxyadenosine; poly(rI).poly(rC)agarose, poly(inosinate).poly(cytidylate) double stranded polynucleotide covalently bound to agarose though poly(rI); HEPES, 4-(2-hydroxyethyl)-1-piperazineethanesulfonic acid; A, adenosine; 3'dA, 3'-deoxyadenosine (3'-deoxyadenylate); pA, 5'-AMP; p3'dA, 3'-deoxy-5'-AMP or 3'-deoxyadenylate; 3'-dATP, 3'-deoxyATP; BAP, bacterial alkaline phosphatase; SVPD, snake venom phosphodiesterase I; ATP; adenosine triphosphate; AMP, adenosine monophosphate.

Under ordinary circumstances a cell will contain ATP and ATP synthetase and an endonuclease which will not interact. In a manner not entirely understood where viral infection of the cell is about to occur interferon reacts upon the cell causing the synthetase to act upon the ATP to form $(2'-5')$oligo(A) having the general designation $(2'-5')$p$_m$A(pA)$_n$ where m is 1,2 or 3 and n may be 1–14, preferably 1–5. Upon intrusion of the virus which contains double stranded ribonucleic acid, the $(2'-5')$ oligo (A) activates the endonuclease which then destroys the messenger ribonucleic acid of the virus, preventing replication of the virus. In this antiviral defense mechanism of the cell, generally speaking, the $(2'-5')$ oligo (A) produced by the cell, is destroyed. The half life of this oligomer is extremely short and cannot therefore be utilized as an externally administered anti viral material without being immediately destroyed by the cell defense mechanisms. It would be desirable therefore to provide an endonuclease activator of substantially greater half life than the $(2'-5')$ oligo (A) which can be administered as a anti-viral material without being immediately destroyed by the cellular defense mechanisms.

The existance of the $(2'-5')$ phosphodiester bond in nature is an item of comparatively recent knowledge (Cory et al *Biochim Biophys Acta* 103, 646 (1965)).

In classical work by Lord Todd it was shown that in the more commonly recognized $(3'-5')$ phosphodiester bond compound a cylic linkage between the 3'-hydroxyl group and the bridging phosphate group between the two ribose moieties was essential for the hydrolytic cleavage of the phosphodiester linkage. It is further known that all reactions involving adenosine triphosphate depend upon the presence of an hydroxyl moiety either in the 2'- or in the 3'-position of the ribose nucleus of the adenosine moiety. In considering the reasons for the rapid destruction of $(2'-5')$ oligo (A) in the cell it will be seen that the 2'- position can not participate since it does not bear a hydroxyl group.

The inventors herein therefore postulated that since the 2'-position was not available for reaction, the degradation of the oligomer might proceed via a cyclic mechanism involving the 3'-hydroxyl in a manner similar to the involvement of the 2'-hydroxyl as shown by Todd. The inventors herein therefore further postulated that the absence of a hydroxyl moiety at the 3'-position might interupt the hydrolytic degradation of the $(2'-5')$ phosphodiester linkage and thus lead to an increased half life for the resulting product. They further postulated that if the presence of the aforesaid 3'-hydroxyl group was *not* essential for the activation of the endonuclease there might be provided a material which would carry out the endonuclease activating function of $(2'-5')$ oligo (A) while having a substantial greater half-life.

Primary exposure to Epstein Barr virus (EBV) in childhood usually results in a silent infection. If infection with EBV is postponed until adolescence, a more serious illness, infectious mononucleosis, develops in approximately 40 percent of the individuals. Although usually thought of as resulting in a self-limiting lymphoproliferative disease, it is becoming increasingly clear that primary infection with EBV can result in life-threatening illness in both adolescents and children. This fact adds support that the morbidity and mortality associated with EBV infection is more serious than originally thought. EBV infection has also been associated with several malignancies, Burkitt's lymphoma and nasopharyngeal carcinoma and Hodgkin's disease.

In vitro systems have been used to evaluate the ability of compounds with antiviral properties to inhibit EBV replication, including 1-β-D-arabinofuranosylthymine and 9-β-D-arabinofuranosyladenine. One of the difficulties encountered with nucleoside analogs as antiviral agents is specificity for the virus-infected cell and concomitant cytotoxicity. Another difficulty with nucleoside analogs (such as 9-(2-hydroxyethoxymethyl)guanine and 5'-amino-5'-deoxyiodouridine) as antiviral agents is that they can act only after the mammalian cell is infected by a virus and the viral deoxythymidine kinase is expressed. Because of these difficulties with the use of nucleosides, interest has grown in the use of autochthonous interferon as an antiviral and antineoplastic agent. However, the development and use of interferon as an antiviral agent has been limited due to scarcity and problems associated with delivery to target cells. Another disadvantage of interferon as an antiviral/antitumor agent is the recent report of the formation of antibodies to interferon. Few in depth in vitro studies have been reported on the effects of purified interferon on EBV replication in human lymphocytes, although fibroblast transformation by oncogenic DNA viruses has been successfully inhibited by exogenously added interferon. It has recently reported that the transformation of adult, but not newborn, lymphocytes by EBV and phytohemagglutinin is inhibited by interferon.

Interferon-treated cells develop the antiviral state by the induction of $(2'-5')(A)_n$ synthetase and a protein kinase. The $(2'-5')A(pA)_n$ formed by the synthetase in the presence of double stranded RNA activates a latent endoribonuclease which degrades messenger RNA. Thus it appeared to the inventors herein that Epstein Barr virus would provide an interesting test model for the aforementioned hypothesis.

SUMMARY OF THE INVENTION

$(2'-5')$-Oligo (3'-deoxyadenylate), an analog of $(2'-5')$-oligo (A) possessing the general structure $p_m3'dA[2'p5'(3'dA)]_n$ where m is 1, 2, or 3 and n is 1, 2, 3, or 4 is synthesized by incubating 3'-dATP with a suitable ATP: $(2'-5')$oligo(A) adenyltransferase in the presence of certain double stranded polynucleotides covalently bound to a support phase. The products of the incubation are purified by chromatographic means. The major products are the trimer triphosphates (m=3, n=2) the tetramer diphosphate (m=2, n=3) and the tetramer triphosphate (m=3, n=3) and the dimer triphosphate (m=3, n=1) the trimer inhibit protein synthesis in lysed rabbit reticulocytes.

The $(2',5')$-oligo (3'-deoxyadenylate) was incubated with a phosphatase effective against terminal phosphate groups but inert with respect to SVPD groups suitably bacterial alkaline or acid phosphatase to provide the corresponding core oligomer analog that is to say, the 3'-deoxyadenosine in place of the 3'-deoxyadenosine polyphosphate.

The core analog oligomer has been found to inhibit the transformation of Epstein Barr virus in human lymphocytes in the absence of interferon and has similarly been found to inhibit replication of Herpes Simplex virus type 1 in human fibroblast monolayers, also in the absence of interferon.

It is the surprising finding herein that while the core analog oligomer $(2'-5')3'dA(2'p5'3'dA)_3$ has the foregoing transformation inhibitory activity as does the natural core oligomer $(2'-5')dA(2'p5'dA)_n$ in contrast to the latter, the former has been found to be non-cytotoxic at the levels tested as well as having a substantially greater half life.

The compounds of the present invention that is to say, compounds having the structure:

may be taken up in pharmaceutically acceptable carriers for example, solutions, suspensions, tablets, capsules, ointments, eloxias, and injectable compositions and the like and administered to subjects suffering from viral infection the dosage administered depending upon the severity of the infection and the size and weight of the infected subject. The compositions may particularly be employed against Epstein Barr virus and herpes simplex infection.

DESCRIPTION OF THE PREFERRED EMBODIMENTS

In the process of the present invention 3'-dATP is incubated with a suitable double stranded polynucleotide covalently bounded to a suitable substrate in the presence of an appropriate ATP: $(2'-5')$oligo (A)adenyltransferase.

The transferase may be isolated from a number of sources suitably from lysed rabbit reticulosites, L cells and HeLa cells. For the transferase to be effective it is important that it be bound to a double stranded polynucleotide. It has been found that poly(rI).poly(rC) in column wherein the material is bound to the substrate, suitably agarose, through the poly(rI). is especially suitable.

Where the transferease is derived from HeLa cells there is utilized the procedure of Baglioni et al (*Biochemistry* 18, 1765-1770 (1979)). Where L cell extract is utilized this is prepared in accordance with the method of Lenz et al (*Biochemistry* 17, 87 (1978)), similarly, when LRR (lysed rabbit reticulocyte) is utilized.

The column wash buffer comprises aqueous potassium chloride, aqueous magnesium acetate, aqueous dithiothreitol, glycerol and HEPES to pH 7.5. The 3'-dATP in the same buffer is charged to the column and the column incubated. Suitably, incubation is carried out at between 25° and 35° C., suitably at about 30° C., for from between 5 to about 25 hours. It has been found that incubation periods exceeding 15 hours are desirable for a reasonable level of conversion. Longer incubation periods have so far not been found to be harmful or leading to degradation of product. If desired, radioactive marker compounds may be utilized to assist in indentification of the desired fraction. For this purpose [8-$^3$H] or [$\alpha$-$^{32}$P] may be utilized as the radioactive markers. A radioactivity of the order of between 500 and 5000 mCi/m mole may be employed for the tritium marker and between 500 and 5000 Ci/m mole for the phosphorus marker. The column is then eluted with the abovementioned column wash buffer. The product is then applied to a DEAE cellulose column and washed therefrom with aqueous potassium chloride suitably between 0.1 and 1 molar. If desired the product may be further purified by chromatography on Sephadex suitably Sephadex G-25.

There is thus obtained the desired $P_m$ 3'dA[2'p5'(3'-dA)]$_n$ where m is 1, 2 or 3 and n is 1,2,3 or 4.

In order to produce the "core analog" the aforementioned oligomer is dephosphorylated at the 5'-position. There may be utilized any phosphatase or combination of phosphatases effective against terminal phosphate groups but inert with respect to phosphodiester groups. Thus, the phosphate groups at the 5'-position would be removed while the phosphate groups bridging between the 2' and 5'-positions of the adjacent ribose nuclei would be unaffected. There may be utilized bacterial alkaline or acid phosphatase of which bacterial alkaline phosphatase is especially preferred. The procedure, however, is not restricted thereto. While BAP will remove all of the phosphate groups at the 5' position this removal may, if desired, be carried out in two stages. Thus, utilizing apyrase, ATPase, pyrophosphatase the outermost two phosphate groups of a triphosphate moiety of the outermost phosphate group of a diphosphate moiety may be removed.

The final phosphate group may then be removed with any phosphatase or any 5'-nucleotidase. In the preferred procedure the (2'-5')oligo (3'-deoxyadenylate) is digested with BAP in a suitable buffer for example, Tris hydrochloride at pH of about 8 for from about 45 to about 120 minutes at from about 30° to about 40° suitably about 37° C. The reaction is terminated by the addition of aqueous urea and the reaction mixture is purified on Sephadex and lyophilized.

Figure 1:
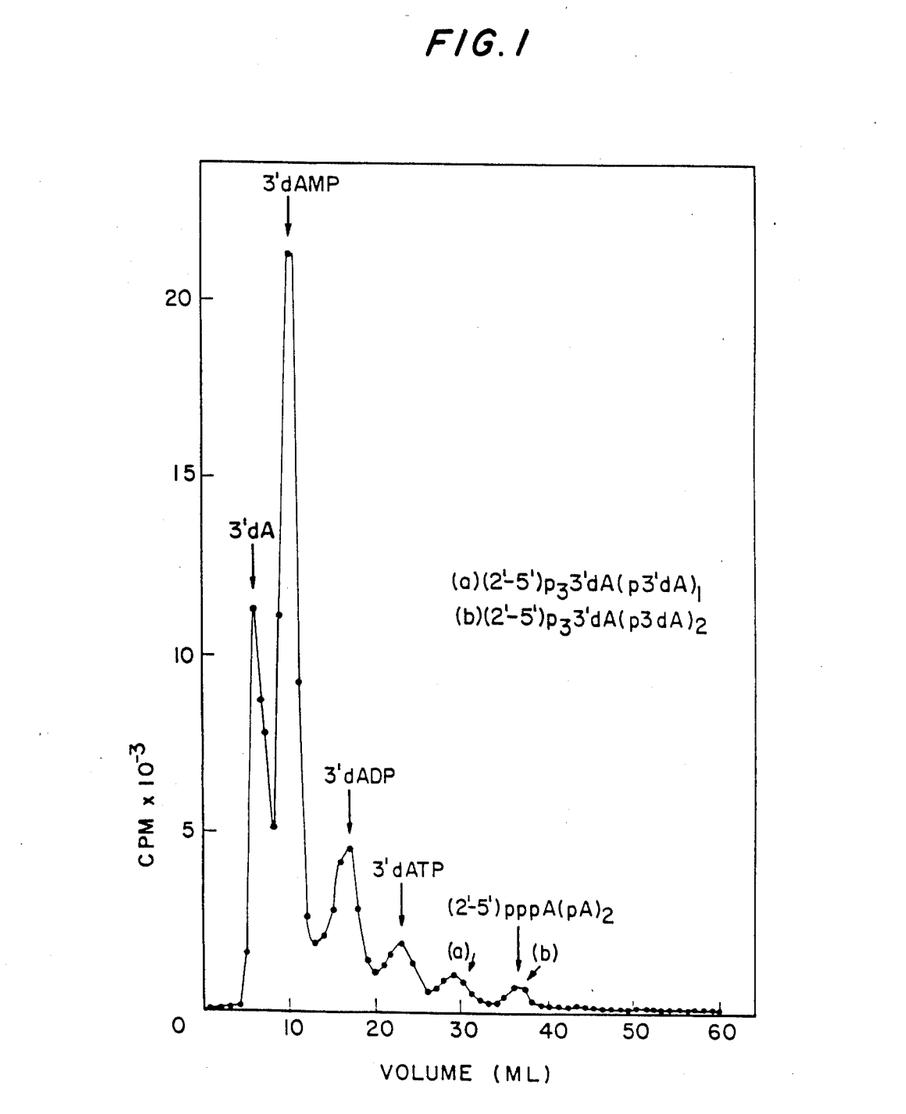
FIG. 1 is a graphical representation of DEAE chromatographic elution of the enzymic oligomerization product with markers.

Several experiments were done to characterize the structure of the putative (2'-5')ppp3'dA(p3'dA)$_2$ and to establish its biological properties. Treatment of the putative [$^{32}$P](2'-5')ppp3'dA(p3'dA)$_2$ with BAP followed by XAD-4 chromatography resulted in the isolation of 34% of the $^{32}$P as $^{32}$P$_i$ (theoretical—33.3%). Additional proof for the structure of (2'-5')ppp3'dA(p3'dA)$_2$ was obtained by treatment of the adenylate analog with BAP, SVPD I, and T2 RNase followed by tlc and measurement of radioactive compounds. The nucleotide synthesized from [$\alpha^{32}$P]3'dATP and purified by DEAE cellulose chromatography (FIG. 1, charge—minus 6) showed only one radioactive spot (FIG. 1,). BAP hydrolysis of the putative [$\alpha$-$^{32}$P](2'-5')ppp3'dA(p3'dA)$_2$ produced $^{32}$P$_i$ ad core [$^{32}$P](2'-5')3'dA(p3'dA)$_2$. There was no $^{32}$P in the region of (2'-5')A(pA)$_3$. Therefore, the putative [$^{32}$P]ppp3'dA(p3'dA)$_2$ was not contaminated with (2'-5')ppA(pA)$_3$ (charge—minus 6). Hydrolysis of core [$^{32}$P]3'dA(p3'dA)$_2$ with SVPD I formed [$^{32}$P]3'dAMP; there was no $^{32}$P in the AMP region. Therefore, the [$\alpha$-$^{32}$P]3'dATP could not be contaminated with [$\alpha$-$^{32}$P]ATP.

Further proof of the 2',5' linkage was obtained by treatment of the putative (2'-5')ppp3'dA(p3'dA)$_2$ by T2 RNase; there was no hydrolysis. Core [$^{32}$P](2'-5')3'dA(p3'dA)$_2$, [$^{32}$P]3'dAMP, and [$^{32}$P](2'-5')ppp3'dA(p3'dA)$_2$ following elution and re-chromatography on cellullose tlc plates in solvent B showed only one radioactive spot each.

The structural characterization is supported by further experiments on the core trimer analog produced by BAP digestion.

On the aforementioned DEAE chromatography, the putative (2'-5')3'dA(p3'dA)$_2$ ran with AMP (charge −2) indicating it too had a charge of −2, which would be correct. The SVPD digestion carried out on [G-$^3$H](2'-5')3'dA(p3'dA)$_2$ showed not only the expected 3'dAMP but also the expected 3'dA, though the latter was not isolated in the quantitatively expected amount.

All references herein cited with respect to synthetic or analytical procedures are incorporated herein by reference.

EXAMPLES

Example I

Cell culture and virus preparation

Heparinized whole venous blood was obtained from the umbilical cords of newborn infants (human umbilical cord lymphocytes) or EBV-seronegative volunteers (peripheral blood lymphocytes) in collaboration with Temple University Hospital, Philadelphia, PA. Mononuclear leukocytes were prepared by the Ficoll-Hypaque method of Boyum (*Scand. J. Clin. Invest.* 21 (Sup. 97), 77 (1968)) and were cultured in RPMI-1640 supplemented with 20% fetal bovine serum as described (Henderson et al, *Virology* 76, 152 (1977)). The lymphoblastoid cell lines BJAB and RAJI were gifts of Drs. Werner and Gertrude Henle, Children's Hospital, University of Pennsylvania, Philadelphia, PA, and were cultured as described above. The lymphoblastoid line C85-5C was obtained by transformation of human umbilical cord lymphocytes following infection with EBV and maintained as described above. Cultured mouse L cells were maintained in minimum essential medium (Eagle) supplemented with Earle's salts, L-glutamine and 6% fetal bovine serum. Interferon-treated mouse L cells were supplied by Dr. Esther H. Chang, National Cancer Institute, NIH. EBV stocks produced from the cottom top marmoset line B95-8, obtained from Dr. George Miller, Yale University, had a TD$_{50}$/0.20 ml of equal to or greater than 10$^4$ as determined on human umbilical cord lymphocytes. EBV stocks were maintained at −70° C. until use. Human umbilical cord lymphocytes and peripheral blood lymphocytes were infected as described (Henderson et al, Supra).

Example II

Enzymatic synthesis and isolation of (2'-5')ppp3'dA(p3'dA)$_n$ in L cell extracts Interferon treated L cell extracts were prepared as described by Lenz et al, *Biochemistry* 17, 80 (1978). Poly(rI). poly(rC)-agarose, packed in a small column (0.5 ml), was washed with 50 ml of buffer A (90 mM KCl, 1.5 mM Mg(OAc)$_2$, 1 mM dithiothreitol, 100 mM HEPES, pH 7.5, 10% glycerol). Interferon-treated L cell extracts (1 ml) were passed through the column and washed with 80 ml of buffer A. A reaction mixture containing 50 mM Mg(OAc)$_2$, 1 mM dithiothreitol, 90 mM KCl, 10 mM HEPES, pH 7.5, 10% glycerol, 5 mM [$\alpha$-$^{32}$P]3'dATP (Amersham/Searle; 2$\mu$ Ci; 3000 Ci/mmol) was added to the column and incubated for 24 hr at 42° C. One ml of water was added to displace the nucleotides. The water was removed by lyophilization and unreacted 3'dATP was converted to 3'dADP by hexokinase (type VII, Sigma Chemical Co.) as described by Dougherty et al, *J. Biol. Chem.* 255 3813 (1980). The reaction products were chromatographed on PEI-cellulose tlc plates (Polygram CEL 300 PEI, Brinkman) in 0.75M potassium phosphate, pH 3.5. One major radioactive area corresponding to 3'dADP was detected. A second radioactive area corresponding to a slower migrating compound was detected and tentatively identified as trimer analog. The putative radioactive trimer analog was eluted from the plate with 1M NH$_4$HCO$_3$, lyophilized, and reconstituted in glass distilled water.

Example III

Oligomer synthesis

Poly(rI). poly(rC)-agarose columns (0.5×1.5 cm) bound with (2'-5') (A)$_n$ synthetase were prepared as described by Baglioni et al (*Biochemistry* 18, 1765 (1979)), except that reticulocyte lysate (1.2 ml) was used in place of HeLa cell extract and the column wash buffer consisted of 100 mM KCl, 2 mM Mg(OAc)$_2$, 2 mM dithiothreitol (DTT), 10% glycerol and 20 mM HEPES, pH 7.5 (buffer A). The final concentration of Mg(OAc)$_2$ was 8 mM in all incubations except for the [G-$^3$H]3'dATP experiment where the concentration was 2.3 mM. Columns were incubated at 30° C. for the time periods indicated with [8-$^3$H]ATP (10 Ci, 22 Ci mmol$^{-1}$), [$\alpha$-$^{32}$P]3'dATP (25 Ci, 640 or 3000 Ci mmol$^{-1}$), or [G-$^3$H]3'dATP (10$\mu$ Ci, 640 mCi mmol$^{-1}$). Ninety five percent of the radioactivity was eluted with 2 ml of buffer A. [$\alpha$-$^{32}$P]3'dATP was purchased from Amersham Corporation (Arlington Heights, IL, USA) and New England Nuclear Corporation (Boston, MA, USA). Cordycepin, (3'-deoxyadensoin), was isolated and purified from *Cordyceps militaris* (mp 228°–229° C., literature 231° C.). Commercially available 3'dATP of the highest purity was purchased from Sigma Chemical Co. (St. Louis, MO, USA) or synthesized (Suhadolnik et al, *J. Biol. Chem.* 252 4125 (1977)). [G-$^3$H]3'dATP was synthesized in the laboratory, oxidized with periodate to remove contaminating ATP or other ribonucleotides and repurified by descending paper chromatography (Whatman 3 MM in solvents A and B; solvent A: isobutyric acid-concentrated ammonia-water, 66:1:33, v/v/v; solvent B: 1-propanol-concentrated ammonia-water, 60:30:10, v/v/v). In solvents A and B, one uv absorbing region or one radioactive region was detected for either 3'd-ATP, [G-$^3$H]3'dATP or [$\alpha$-$^{32}$P]3'dATP. The ratio of tritium in the adenine:3-deoxyribose of the [G-$^3$H] cordycepin was 9:1. Product formation was determined by the amount of radioactivity displaced from the DEAE cellulose column with 0.35M KCl divided by the total radioactivity recovered, except for the [G-$^3$H]3'dATP experiment. Percent conversion for the [G-$^3$H]3'dATP experiment was determined from the elution profile shown in FIG. 1 as the percentage of radioactivity eluting after 3'dATP because chromatography of this material on DEAE cellulose and elution with 0.35M KCl was not performed prior to the DEAE cellulose chromatography NaCl gradient elution method shown in FIG. 1. The amount of $^{32}$P displaced with 0.35M KCl when 25$\mu$ Ci of [$\alpha$-$^{32}$P]3'dATP was added to DEAE cellulose columns was 0.15%, which was subtracted from the $^{32}$P in the 0.35M KCl fraction.

The total product obtained comprises product where m=3 and n=1 and 2 predominantly.

In accordance with the above procedure oligomers wherein n=3 or 4 may also be obtained in lesser amounts.

Chromatography of the analog, [$^3$H](2'-5')p$_m$3'dA(p3'dA)$_n$, from incubations with [G-$^3$H]3'dATP on DEAE cellulose.

Peak fractions of material washed from poly(rI).-poly(rC)-agarose columns from a 17 h incubation with [G-$^3$H]3'dATP were applied to a DEAE cellulose column (Whatman DE52, 0.5×17 cm). The nucleotides were displaced with a 50–150 mM linear gradient of NaCl (40 ml/40 ml), 50 mM tris-HCl, pH 8.0 in 7M urea; 1 ml fractions were collected; flow rate: 4 ml h$^{-1}$. Cordycepin (3'dA), 3'dAMP, 3'dADP, 3'dATP, and authentic (2'-5')pppA(pA)$_2$ were included as markers and were monitored on a recording spectrophotometer (LKB 2138 Uvicord S). In the other incubations with [$\alpha$-$^{32}$P]3'dATP and [8-$^3$H]ATP, the radioactive material eluting from the poly(rI).poly(rC)-agarose columns were chromatographed on DEAE cellulose columns (0.6×2.0 cm) and washed with 42 ml of buffer B: 0.09M KCl, 20 mM HEPES, pH 7.5. The oligonucleotides were displaced with 5 ml of buffer B supplemented with 0.35M KCl. The radioactive nucleotides in the 0.35M KCl were further fractionated by the 7M urea-NaCl gradient-DEAE cellulose chromatography method described above.

The peak for (2'-5')p$_m$3'dA(p3'dA)$_n$ where m=3 n=1 precedes that where m=3, n=2, the latter running at the same rate as the corresponding 3'-hydroxylated oligomer.

In accordance with the above procedure, but where, in place of L cell extracts there are utilized HeLa cell extracts, the same product is obtained.

TABLE 1

Enzymatic Synthesis of (2'-5')p$_m$3'dA(p3'dA)$_n$ and (2'-5')pppA(pA)$_n$

| Substrate | Final concentration (mM) | Incubation time (h) | Conversion to (2'-5') oligonucleotide (%) |
|---|---|---|---|
| [8-$^3$H]ATP | 2 | 5 | 21.9 |
| [8-$^3$H]ATP | 2 | 17 | 19.0 |
| [$\alpha$-$^{32}$P]3'dATP | 2 | 5 | 0.3 |
| [$\alpha$-$^{32}$P]3'dATP | 2 | 17 | 3.0 |
| [G-$^3$H]3'dATP | 1.3 | 17 | 3.7 |

Example IV

Enzymatic dephosphorylation of $(2'-5')p_m3'dA(p3'dA)_m$ $(2'-5')p_33'dA(p3'dA)_3$ (1.2 μM) were digested with bacterial alkaline phosphatase (0.28 mg) in Tris hydrochloride (58 mM, 0.5 ml, pH 8.0) for 90 minutes at 37° C. The digestion was terminated by the addition of urea (7M, 3 ml) and the reaction mixture washed through a sephadex G10 column with buffer A. The elution was followed by UV analysis at 260 nM and the peak material lyophylised to yield the desired $(2'-5')3'dA(p3'dA)_3$. In accordance with the above procedure, but where m is 1 or 2 and n is 1, 2, 3 or 4, there is obtained the corresponding 5'-dephosphorylated oligomer having an unchanged n value respectively.

In accordance with the foregoing procedure, but where, in place of bacterial alkaline phosphatase, there is utilized bacterial acid phosphatase at pH 8, there are obtained the same products.

In accordance with the foregoing procedure, but where, in place of bacterial alkaline phosphatase, there is utilized apyrase, ATPase, or pyrophosphatase, there is obtained the corresponding $(2'-5')p3'dA(p3'dA)_n$ further digestion with 5'-nucleotides or any phosphatase there is obtained the corresponding 5'-dephosphorylated oligomer.

Example V

Characterization of $(2'-5')ppp3'dA(p3'dA)_n$ $[^{32}P](2'-5')ppp3'dA(p3'dA)_n$ chromatographically pure, showed resistance to hydrolysis by T2 ribonuclease which is evidence for the (2'-5') linkage. Treatment of $[^{32}P](2'-5')ppp3'dA(p3'dA)_n$ with bacterial alkaline phosphatase produced $^{32}P_i$ and core trimer analog $((2'-5')3'dA(p3'dA)_n)$. No radioactivity was detected in the core trimer region. Snake venom phosphodiesterase treatment of $[^{32}P](2'-5')ppp3'dA(p3'dA)_n$ yielded only $[^{32}P]3'dAMP$. No radioactivity was detected in the AMP region. At 100 nM the trimer analog inhibited translation 80% in lysed rabbit reticuloytes, while the inhibition by 100 nM authentic trimer was approximately 20%.

BIOLOGICAL ACTIVITY

The inhibition of translation by the analog, $(2'-5')ppp3'dA(p3'dA)_2$, was compared with the inhibition by tetramer adenylate, $(2'-5')pppA(pA)_3$, and the trimer adenylate, $(2'-5')pppA(pA)_2$. The inhibition of translation by 40 nM $(2'-5')pppA(pA)_3$ was 52% and decreased to control values at 0.004 mM; the inhibition of translation by 22 nM $(2'-5')ppp3'dA(p3'dA)_2$ was 68% and decreased to control values at 0.04 nM. The trimer analog, $(2'-5')ppp3'dA(p3'dA)_2$, is about four times more potent an inhibitor of translation than is $(2'-5')pppA(pA)_2$.

Figure 2:
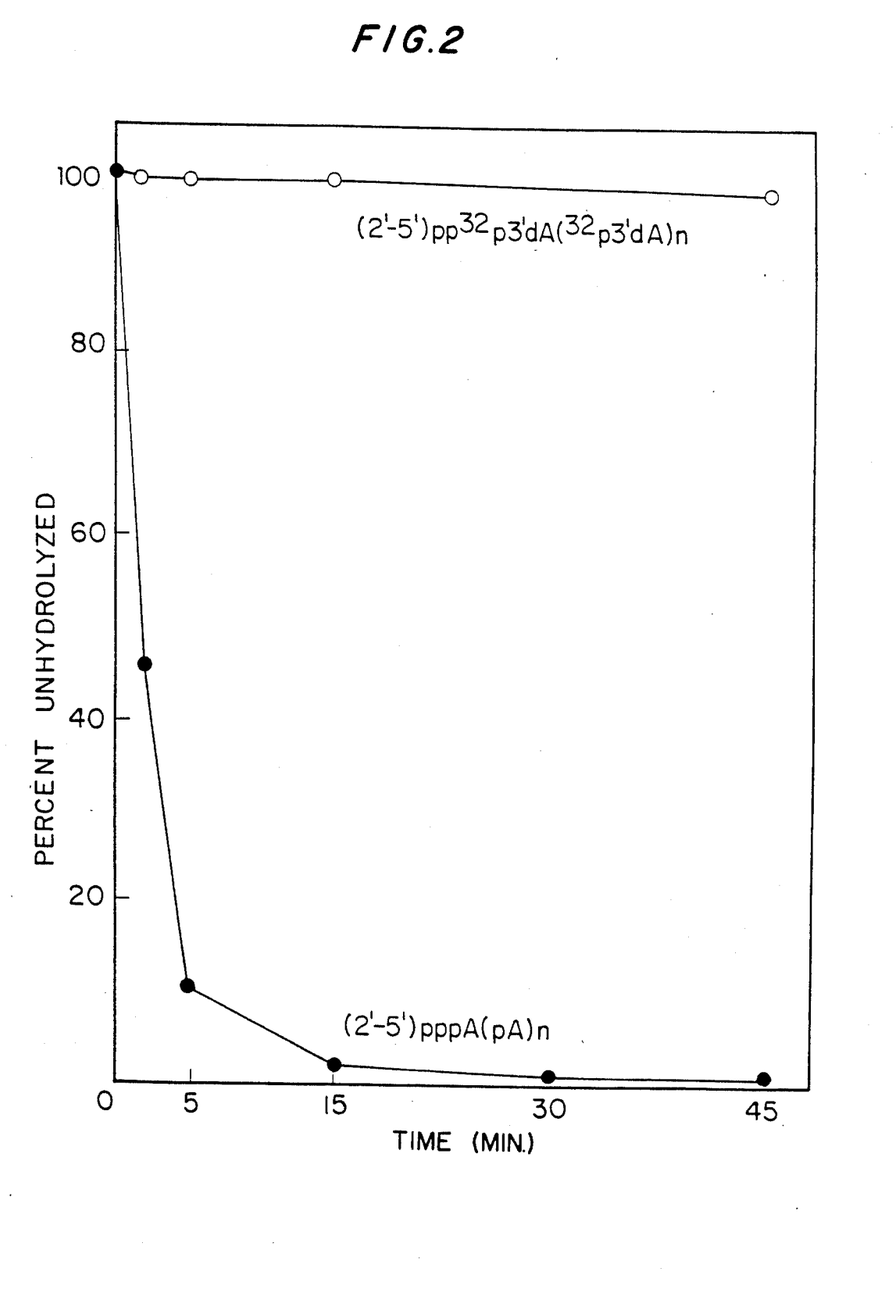
FIG. 2 is a stability representation of $(2'-5')p_3A(pA)_n$ and $(2'-5')p_33'dA(p3'dA)_n$ in HeLa cell extracts.
Figure 3:
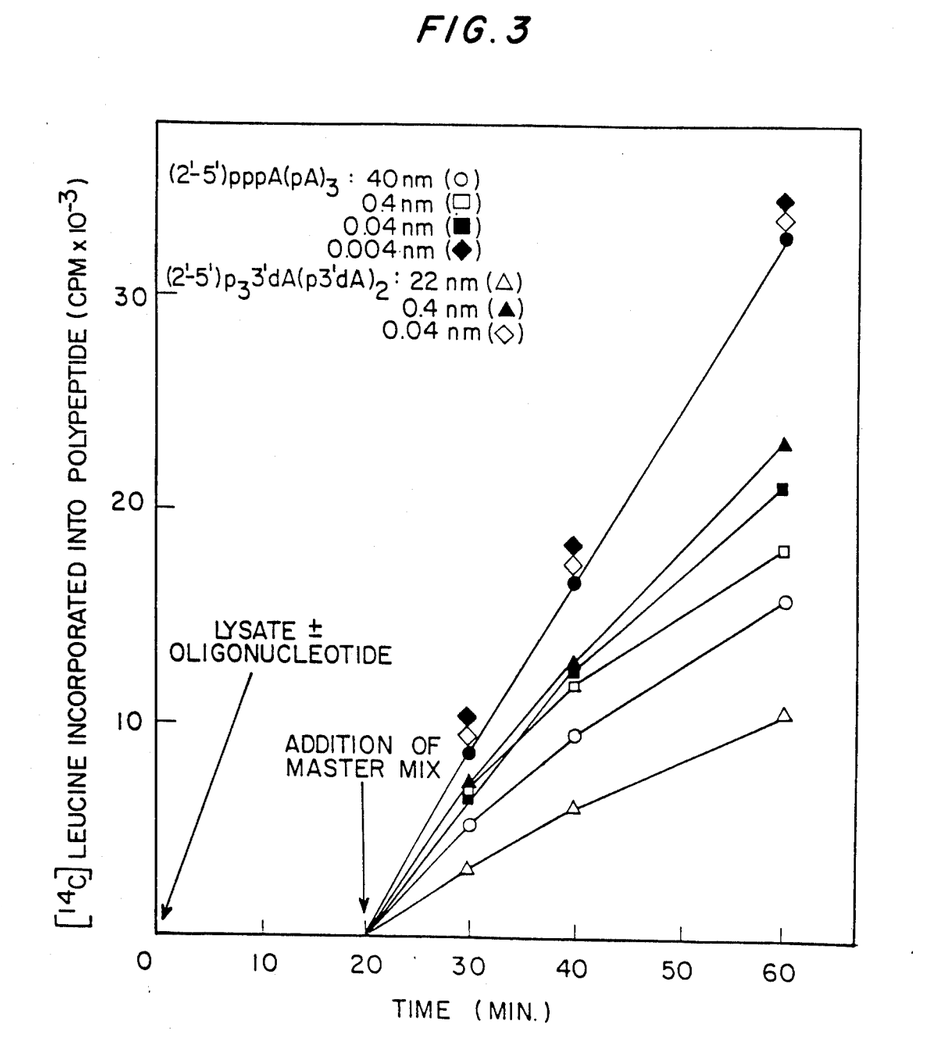
FIG. 3 is a graphical representation of inhibition of Leucine translation.

The stability of $(2'-5')ppp3'dA(p3'dA)_n$ in HeLa cell extracts was compared to that of $(2'-5')pppA(pA)_n$. There was no hydrolysis of the analog, $(2'-5')ppp3'dA(p3'dA)_n$ (12 μM), by HeLa cell extracts folowing a 45 min incubation; however, the $t_{\frac{1}{2}}$ of $(2'-5')pppA(pA)_n$ (5 μM) is about 2 min (FIG. 2). With 500 μM $(2'-5')pppA(pA)_n$, there was a 50% hydrolysis in 45 min as determined by DEAE cellulose chromatography; with 500 μM authentic core analog, $(2'-5')3'dA(p3'-dA)_2$, there was no hydrolysis as determined by cellulose tlc (solvents A and B). Neither cordycepin nor 3'dAMP was detected. The lack of hydrolysis of the analog may be similar to the lack of hydrolysis of (3'-5')2'-deoxyoligonucleotides by the 2',5'-phosphodiesterase.

The antiviral properties of 5'-dephosphorylated "core" $(2'-5')A(pA)_2$, $(2'-5')A(pA)_3$ and $(2'-5')3'dA(p3'-dA)_2$ were compared to the antiviral properties of IFN-α and IFN-β. The (2'-5')oligonucleotides and interferons inhibited Epstein-Barr Virus (EBV)-induced stimulation of DNA synthesis in EBV infected human lymphocytes. Whereas $(2'-5')A(pA)_2$ and $(2'-5')A(pA)_3$ were potent inhibitors of DNA synthesis of infected and uninfected lymphocytes, $(2'-5')3'dA(p3'dA)_2$ inhibited only viral-induced DNA synthesis. The "core" 3'-deoxy (2'-5') oligonucleotide analog inhibited EBV-induced morphological transformation of lymphocytes much the same as "core" $(2'-5')A(pA)_2$ and $(2'-5')A(pA)_3$. $(2'-5')A(pA)_2$ (>300 μM) and $(2'-5')A(pA)_3$ (>150 μM) were toxic to the lymphoblastoid lines Raji and BJAB whereas no toxicity was observed for $(2'-5')3'dA(p3'dA)_2$ (determined by inhibition of colony formation).

Effects on IFN-β and (2'-5')Oligonucleotides of Herpes Simplex Virus Type 1 (HSV-1) Replication (2'-5')- and $(3'-5')A(pA)_3$ have been reported to be taken up by intact lymphocytes. Therefore, we employed an infected centers assay utilizing lymphocytes to determine the ability of (2'-5') oligonucleotides to inhibit HSV-1. After incubation for 72 hr with or without (2'-5')oligonucleotides, leukocytes exposed to HSV-1 were plated onto human foreskin fibroblast monolayers (Table 2). Leukocytes not treated with IFN-β or (2'-5')oligonucleotides developed as infected centers, whereas the fibroblast monolayers onto which IFN-β-treated leukocytes were plated developed significantly less cytopathic effects and then only when higher infected cell concentrations ($>6.7 \times 10^5$ infected cells) were plated onto the fibroblast monolayers. Monolayers exposed to uninfected fibroblasts did not develop cytopathic effects (cpe). $(2'-5')A(pA)_2$ and $(2'-5')A(pA)_3$ inhibited the development of cpe, with significant cpe observed only with fibroblasts treated with $2 \times 10^5$ infected cells. $(2'-5')3'dA(p3'dA)_2$ was less effective in inhibiting the development of cpe from infected leukocytes compared to IFN-β, $(2'-5')A(pA)_2$, and $(2'-5')A(pA)_3$.

TABLE 2

Effect of IFN-β and (2'-5')oligonucleotides on development of infected centers from HSV-1 infected leukocytes as determined by cytopathic effects (cpe) using human foreskin fibroblasts as indicators

| Treatment | cpe at given number of HSV-exposed leukocytes per cell | | |
|---|---|---|---|
| | $2 \times 10^5$ | $6.7 \times 10^4$ | $2.2 \times 10^4$ |
| None (control) | +++ | ++ | + |
| IFN-β (25 U/ml) | ++ | + | 0 |
| (100 U/ml) | +++ | 0 | 0 |
| (250 U/ml) | + | 0 | 0 |
| (500 U/ml) | 0 | 0 | 0 |
| (2'-5')A(pA)₂ (10 μM) | +++ | ++ | 0 |
| (50 μM) | ++ | ++ | 0 |
| (75 μM) | ++ | 0 | 0 |
| (150 μM) | +. | 0 | 0 |
| (2'-5')A(pA)₃ (10 μM) | ++ | + | 0 |
| (50 μM) | + | 0 | 0 |
| (75 μM) | ++ | 0 | 0 |
| (150 μM) | + | 0 | 0 |
| (2'-5')3'dA(p3'dA)₂ (10 μM) | +++ | ++ | + |
| (50 μM) | ++ | ++ | + |

TABLE 2-continued

Effect of IFN-β and (2'-5')oligonucleotides on development of infected centers from HSV-1 infected leukocytes as determined by cytopathic effects (cpe) using human foreskin fibroblasts as indicators

| Treatment | cpe at given number of HSV-exposed leukocytes per cell | | |
|---|---|---|---|
| | $2 \times 10^5$ | $6.7 \times 10^4$ | $2.2 \times 10^4$ |
| (75 μM) | ++ | + | 0 |
| (150 μM) | — | — | 0 |
| (3'-5')A(pA)$_2$ (300 μM) | +++ | 0 | 0 |

+++ = complete destruction of the monolayer
++ = multiple foci of cpe
+ = one focus of cpe
0 = no monolayer disturbances

Effect of Interferon and (2'-5')Oligonucleotides on Lymphoblastoid Cell Survival IFN-α, core trimer, core tetramer, and core pentamer have been reported to inhibit DNA synthesis in concanavalin A stimulated mouse spleen lymphocytes. Therefore, the effect of these agents on colony formation in closely related lymphoblastoid cell lines was determined (Table 3). IFN-β and IFN-B had no appreciable effect on lymphoblast colony formation. (2'-5')A(pA)$_2$ at high concentrations (150-300 μM) and (2'-5')A(pA)$_3$ (50-150 μM) were found to be toxic to BJAB and Raji lymphoblasts. However, the (2'-5')3'dA(p3'dA)$_3$ was not cytotoxic to either BJAB or Raji lymphoblasts at concentrations up to 300 μM. The natural (3'-5')A(pA)$_2$ also found non-cytotoxic does not inhibit transformation either and can be classed as inactive. Therefore, based on the concentrations of (2'-5')oligonucleotides required to produce cytotoxicity in lymphoblasts, the inhibition of EBV-induced transformation by interferon, core trimer, core trimer analog, and to a lesser extent, core tetramer, was not the result of lymphocyte killing by these compounds.

TABLE 3

Cytotoxic effect of IFN-α, IFN-β, and oligonucleotides on established lymphoblastoid cell lines*

| | Concentration at which colony formation was inhibited by greater than 50 percent | | |
|---|---|---|---|
| | Cell line | | |
| Compound | BJAB | Raji | C85-5C |
| (2'-5')A(pA)$_2$ | 150-300 μM | 300 μM | ND |
| (2'-5')A(pA)$_3$ | 150 μM | 50 μM | ND |
| (2'-5')3'dA(p3'dA)$_2$ | >300 μM | >300 μM | ND |
| (3'-5')A(pA)$_2$ | >300 μM | >300 μM | ND |
| IFN-α | ND | ND | >1000 U/ml |
| IFN-β | >500 U/ml | >500 U/ml | >1000 U/ml |

*Determined by colony formation in microtiter plates following treatment with compound for 7 days.
ND = not determined.

We claim:

1. A method of preparing a compound of the formula wherein m is 0, 1, 2 or 3 and n is 0, 1, 2, 3 or 4, wherein m is other than 0 which comprises incubating 3'-deoxyadenosine triphosphate with adenosine triphosphate: (2'-5') oligo(adenosine)adenyltransferase (EC 2.7.7.-) bound to an inert support carrying double stranded polynucleotide.

2. A method of claim 1 wherein the transferase is derived from lysed rabbit reticulocytes, L cells or HeLa cells.

3. A method of claim 1 wherein the transferase is bound to poly(inosinate).poly(cytidylate) double stranded polynucleotide covalently bound to agarose through poly(inosinate).

4. A method of preparing a compound of the formula wherein m is 0, 1, 2 or 3 and n is 0, 1, 2, 3 or 4, wherein m is 0 which comprises digesting a compound of said formula wherein m is other than 0 with a phosphatase effective against terminal phosphate groups but inert with respect to phosphodiester groups.

5. A method of claim 4 wherein the phosphatase is bacterial alkaline or acid phosphatase.

6. A method of claim 2 wherein the transferase is bound to poly(inosinate).poly(cytidylate) double stranded polynucleotide covalently bound to agarose through poly(inosinate).

* * * * *

UNITED STATES PATENT AND TRADEMARK OFFICE
CERTIFICATE OF CORRECTION

PATENT NO. : 4,708,935

DATED : November 24, 1987

INVENTOR(S) : Robert J. Suhadolnik, et al.

It is certified that error appears in the above-identified patent and that said Letters Patent is hereby corrected as shown below: On The Title Page:

In the Title: "(2-5')" should read as --(2'-5')--

In the Abstract, line 5: "straded" should read as --stranded--

Column 2, line 39: "throught" should read as --thought--

Column 3, line 33: "respect to SVPD groups" should read as --respect to phosphodiester groups--

Column 5, line 61: "(p3'dA,$_2$)" should read as --(p3'dA)$_2$--

Column 9, line 25: "5'-nucleotides" should read as --5'-nucleotidase--

Column 9, line 62: "folowing" should read as --following--

Signed and Sealed this

Twenty-fifth Day of October, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,708,935

DATED : November 24, 1987

INVENTOR(S) : Robert J. Suhadolnik, et al.

It is certified that error appears in the above-identified patent and that said Letters Patent is hereby corrected as shown below:

Column 10, lines 3-4: "phosphodiesterease" should read as --phosphodiesterase--

UNITED STATES PATENT AND TRADEMARK OFFICE
CERTIFICATE OF CORRECTION

PATENT NO. : 4,708,935

DATED : November 24, 1987

INVENTOR(S) : Robert J. Suhadolnik, et al.

It is certified that error appears in the above-identified patent and that said Letters Patent is hereby corrected as shown below:

Column 3, line 65:

Column 4, line 18:

Column 4, line 33:

Column 12, line 13:

Column 13, line 30:

Column 14, line 30:

should read as:

UNITED STATES PATENT AND TRADEMARK OFFICE
CERTIFICATE OF CORRECTION

PATENT NO. : 4,708,935
DATED : November 24, 1987
INVENTOR(S) : Robert J. Suhadolnik, et al.

It is certified that error appears in the above-identified patent and that said Letters Patent is hereby corrected as shown below: